United States Patent [19]
Chernyak

[11] Patent Number: 6,005,242
[45] Date of Patent: *Dec. 21, 1999

[54] ENVIRONMENTAL MEDIA AND PRESSURE SENSOR

[75] Inventor: Alex H. Chernyak, San Francisco, Calif.

[73] Assignee: Alconi Sensline, San Fancisco, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/911,959

[22] Filed: Aug. 15, 1997

[51] Int. Cl.$^6$ ....................................................... G01L 9/00
[52] U.S. Cl. ...................... 250/227.14; 250/577; 73/705; 73/714
[58] Field of Search ............................... 250/227.14, 577, 250/574, 231.19; 73/705, 714

[56] References Cited

U.S. PATENT DOCUMENTS

| | | | |
|---|---|---|---|
| 4,691,709 | 9/1987 | Cohen | 128/667 |
| 4,986,671 | 1/1991 | Sun et al. | 374/131 |
| 5,005,005 | 4/1991 | Brossia et al. | 340/604 |
| 5,200,628 | 4/1993 | Ikeda et al. | 250/574 |
| 5,362,971 | 11/1994 | McMahon et al. | 250/577 |
| 5,385,053 | 1/1995 | Wlodarczyk | 73/705 |
| 5,425,273 | 6/1995 | Chevalier | 73/705 |
| 5,469,749 | 11/1995 | Shimada et al. | 73/861.47 |
| 5,606,170 | 2/1997 | Saaski et al. | 250/458.1 |
| 5,781,008 | 7/1998 | Muller et al. | 324/230 |

*Primary Examiner*—Edward P. Westin
*Assistant Examiner*—Thanh X. Luu
*Attorney, Agent, or Firm*—Lumen Intellectual Property Services

[57] ABSTRACT

A sensor for detecting environmental media and pressure comprises two types of optical fibers. An intrinsic fiber containing a portion of the fiber with the jacket removed is sensitive to its surroundings as some light traveling through the fiber will escape. The change in light intensity is received by a light detector, and this information is interpreted to correspond to a certain media, a change in media, or a phase change in media. An extrinsic fiber with a membrane and mirror located at one end is placed vertically in the media. Pressure from the media changes the position of the membrane and the mirror, resulting in a change in the intensity of the light reflected back through the fiber to the light detector. The pressure can then be used to determine the volume of the media in the container. Pressure determination can be continuous. In addition, both types of sensors can be networked, allowing information from one sensor to influence the gathering of information from the other. Both sensors are housed in a durable container, which is connected to the light source and light detector. The container has protective grooves with concave shapes, which prevents accidental damage to the fragile fibers.

10 Claims, 8 Drawing Sheets

ENVIRONMENTAL MEDIA AND PRESSURE SENSOR

FIELD OF THE INVENTION

This invention relates generally to environmental sensors. More particularly, it relates to a sensor for detecting environmental media and pressure which can also determine environmental level and volume measurements.

BACKGROUND OF THE INVENTION

Optical fibers have been used in many types of sensing devices to detect specific media, phase changes in media, and media pressure. For example, the medical field uses fiber optics to measure the intravascular blood pressure of patients. The automotive industry employs fiber optic pressure sensors to measure pressure inside internal engine combustion chambers. In addition, the oil industry makes use of fiber optics to analyze the contents and pressure of oil and gas tanks, as well as oil wells.

Typically, such devices consist of a light source, such as a laser, and a light detector, such as a charge coupled device, connected by an optical fiber. Light from the light source is continuously transmitted through the fiber to the sensor. At the sensor, the light is affected by the media, resulting in a change in light intensity or power. The light then travels to the light detector, where the change in intensity or power is interpreted. The information is then displayed to the user.

Usually, an optical fiber consists of a core and cladding surrounded by a jacket. The jacket functions as a protective barrier, as it does not permit light from the core of the fiber to pass into the environment nor light from the environment to pass into the core. Thus, a jacket ensures that an optical fiber will have almost complete total internal reflection, with minimal light loss due to transmission through the jacket.

How the light is affected at the sensor depends on how the optical fiber is used. Optical fibers can be used extrinsically or intrinsically. Intrinsic fibers are active components of the sensor as their main characteristic, total internal reflection, is altered.

For intrinsic fibers, a portion of the jacket is stripped away, allowing a small amount of light transmission through the cladding or core. The resulting decrease in light intensity or power can be measured by finding the difference between the intensity of the light emitted by the light source and the intensity of the light received at the light detector. The amount of light lost corresponds to a change in the environment, such as a change in media or a change in phase of the same media. An intrinsic fiber sensor may be placed between two normally jacketed optical fibers, or it may be placed at the end of a normally jacketed optical fiber, depending on the user's needs.

Extrinsic fibers are used to detect changes in environmental pressure. They comprise unaltered optical fibers that have a membrane and a reflecting device, such as a mirror, at one end. The fiber is typically positioned vertically, with the membrane and mirror located at the bottom end. Light from the light source travels down the length of the fiber until it encounters the mirror, where it is reflected. The jacket is not removed from any part of the fiber, so total internal reflection is maintained. The sensor is usually lowered into the environment to be analyzed. At increasing depth, the upward pressure increases and the membrane is deformed. The change in position of the membrane causes a change in the position of the mirror. When light from the light source travels down the optical fiber, it will hit the mirror and be reflected back at an angle corresponding to the deformation of the membrane and hence the pressure. The change in reflection angle results in scattering of light and thus a variation in the intensity of the light that is reflected back to the light detector. Using information about the pressure of a medium allows the user to calculate the depth. If the dimensions of the container holding the medium are known, the volume can easily be calculated.

U.S. Pat. No. 5,005,005 by Brossia et al. discloses a sensor to detect environmental media and pressure which makes use of two intrinsic optical fibers. One sensor comprises an unjacketed part of optical fiber between two jacketed parts. This sensor is capable of distinguishing between phases, such as water and ice, and different substances, such as water and gasoline. The second sensor is similar to the first except that it contains a number of unjacketed fiber optic segments and it is placed vertically in the substance to be analyzed. This sensor is capable of distinguishing volume, as the depth and change of depth of the substance is sensed by the number and position of sensors in contact with the substance.

U.S. Pat. No. 5,362,971 by McMahon et al. discloses a fiber optic detection system with an intrinsic fiber sensor in a U-shaped configuration. With such a fiber optic loop, the amount of light lost can be determined by the degree of curvature of the loop. The diameter of this loop can be predetermined to provide optimum results for each substance to be analyzed. In addition, the loop improves compactness.

U.S. Pat. No. 5,606,170 by Saaski et al. discloses a multifunctional sensor system which uses a number of optical fibers to detect environmental media. Of interest is the use of numerous fibers in different patterns to transmit light to and from the sensor.

U.S. Pat. No. 5,385,053 by Wlodarczyk et al. describes a fiber optic pressure system which makes use of an external sensor intended for use in the automotive industry. In this invention, the deformable membrane is less sensitive to higher temperatures, which can distort pressure readings.

Finally, U.S. Pat. No. 5,425,273 by Chevalier discloses a fiber optic pressure system with inclusions in a compressible transparent material. The pressure sensors comprise optical fibers surrounded by a material which is essentially elastic to deformation and is optically transparent to the wavelengths of light used. At least two sensors are used. The distance between the sensors varies when the length between them is deformed. This, in turn, modifies the focal length of the defined optical system and leads to a variation in the light energy collected by a light detector.

None of the above inventions combine the two types of sensors, intrinsic and extrinsic, to design a detector which has the ability to detect both environmental media and pressure. U.S. Pat. No. 5,005,005 can detect the relative level of a fluid in a container, which can be used with other measurements to determine volume; however, it cannot detect the pressure of a fluid.

In addition, no mention is made of protecting the fragile optical fibers which are exposed. The sensors are often lowered to great depths into tanks and in the process the fibers frequently hit against the tank walls. In the case of the oil industry, which produces highly flammable products, the sensing devices are thus vulnerable to explosions. Over and above such major hazards, minor damage to the fibers can result in changes in light reflected or transmitted, which leads to faulty readings.

OBJECTS AND ADVANTAGES OF THE INVENTION

Accordingly, it is a primary object of the present invention to provide sensors to detect both environmental media and their pressure integrated into one device. It is another object of the invention to use environmental pressure information to determine the level of fluid in a container. It is another object of the invention to use environmental pressure information to determine the volume of fluid in a container. Yet another object of the invention is to allow continuous calculations of these measurements. A further object of the invention is to network the environmental media information and environmental pressure information to allow one type of information to influence gathering of the other. A sixth object of the invention is to provide a durable protective housing for such types of sensors to reduce the chance of damage. A seventh object of the invention is to provide an inexpensive, small, flexible, and highly durable media and pressure sensor.

SUMMARY OF THE INVENTION

These objects and advantages are attained by a device for detecting environmental media and pressure, which can also be used for environmental level and volume measurements. The device is comprised of a light source and a light detector connected by two optical fibers, one fiber for sensing environmental media, the other for sensing environmental pressure. The fiber for sensing environmental media comprises an unsheathed loop of a certain diameter. The intensity of light passing through this unjacketed loop will decrease depending on the environmental media to which the loop is exposed. The difference in intensity between the light emitted by the light source and the light received by the light detector then referenced to a corresponding medium. The fiber for sensing the pressure of the environmental media has a membrane and a mirror at one end. As the sensor is immersed in the media to be measured, the position of the membrane changes as the pressure increases, causing a change in the position of the mirror as well. Thus, light traveling along the fiber will hit the mirror at a different angle and cause a varying degree of scattering. The return light will have a different intensity than before the pressure change. This difference can then be used to determine the media pressure. The media pressure will allow the user to calculate the level of the media. Information about the dimensions of the container holding the media then allows calculation of the volume of the media. All measurements by the media and pressure sensors can be achieved continuously. In addition, information from each sensor can be used to influence the gathering of information from the other sensor. The housing described in the present invention comprises curved edges and protective recessed grooves for each sensor. The design of the housing decreases the chance that the fragile sensors will be damaged should the device be dropped, hit the side of a container, or encounter a physical obstacle.

DETAILED DESCRIPTION

Figure 1:
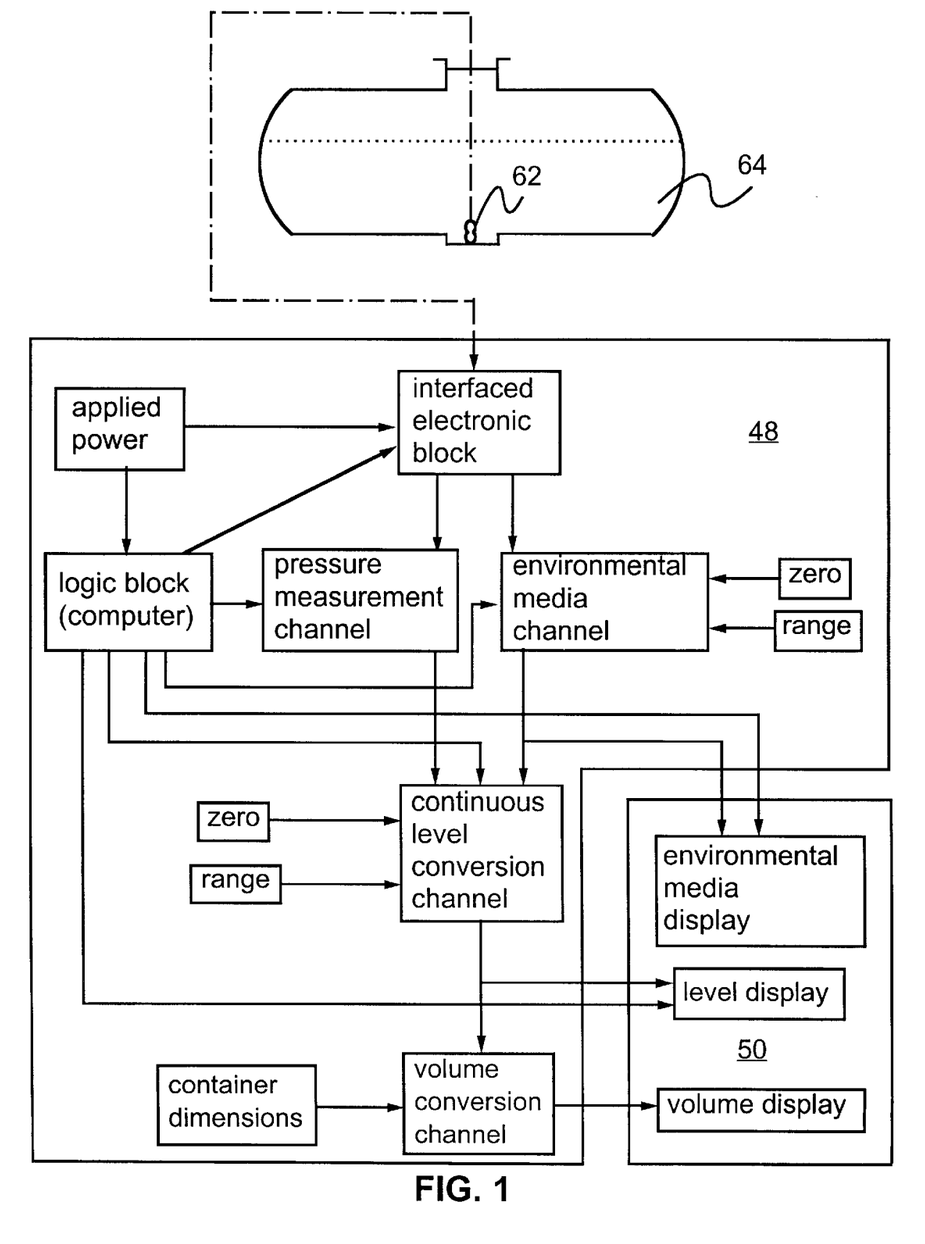
FIG. 1 is a block diagram illustrating the present invention.

The preferred embodiment of the present invention is illustrated in the block diagram of FIG. 1. A sensor device 62 is placed on the bottom of a tank 64 containing a liquid medium, such as gasoline. The sensing component of sensor device 62 comprises an optical fiber with a media sensor and an optical fiber with a pressure sensor, both contained within a housing. One end of the sensing component is connected to at least one optical fiber, which runs out an opening of tank 64 to an interfaced electronic block. The interfaced electronic block receives the media sensor and pressure sensor light signals from the optical fiber, calculates their intensities, and relays the information to the environmental measurement channel and the pressure media channel, respectively.

Figure 5:
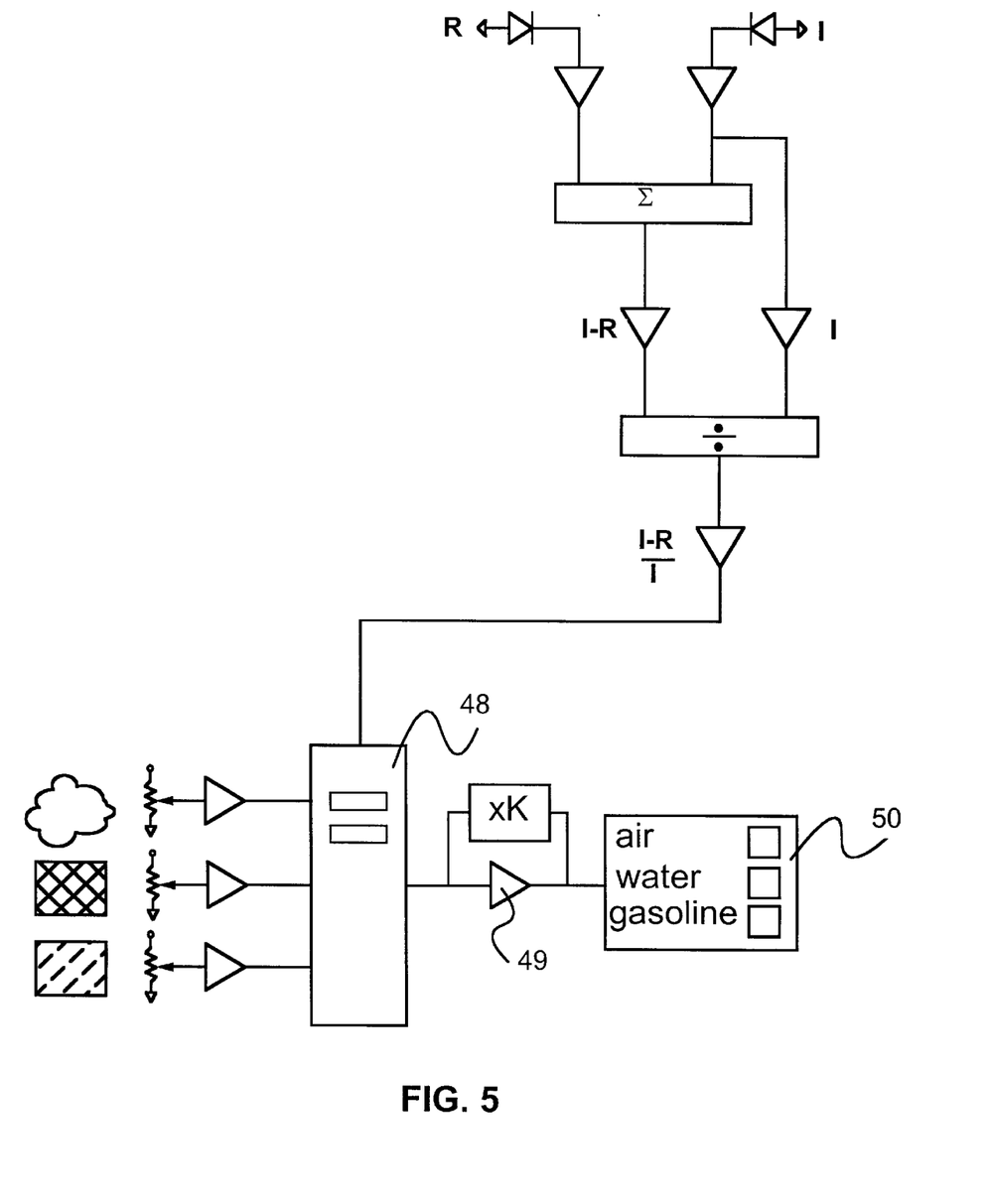
FIG. 5 is a diagram of the media recognition channel.

The environmental media channel calculates the difference in intensity of the light signal emitted by the light source and the light signal detected by the light detector for the environmental media sensor. The calculated value, as determined from a range of values, is then referenced against known values for different medium, as shown in FIG. 5. When the media has been identified, it is displayed on the environmental media display 50.

The pressure measurement channel also calculates the difference in intensity of the light signal emitted by the light source and the light signal detected by the light detector for the environmental pressure sensor. The calculated value, as determined from a range of values, is sent to the continuous level conversion channel. Along with the media identification from the environmental media channel, the calculated value is used to determine the level of the medium. The level of the medium is displayed on the level display. The level of the medium, along with the container dimensions, allows calculation of the volume of the medium. The volume of the medium is also displayed.

Figure 2:
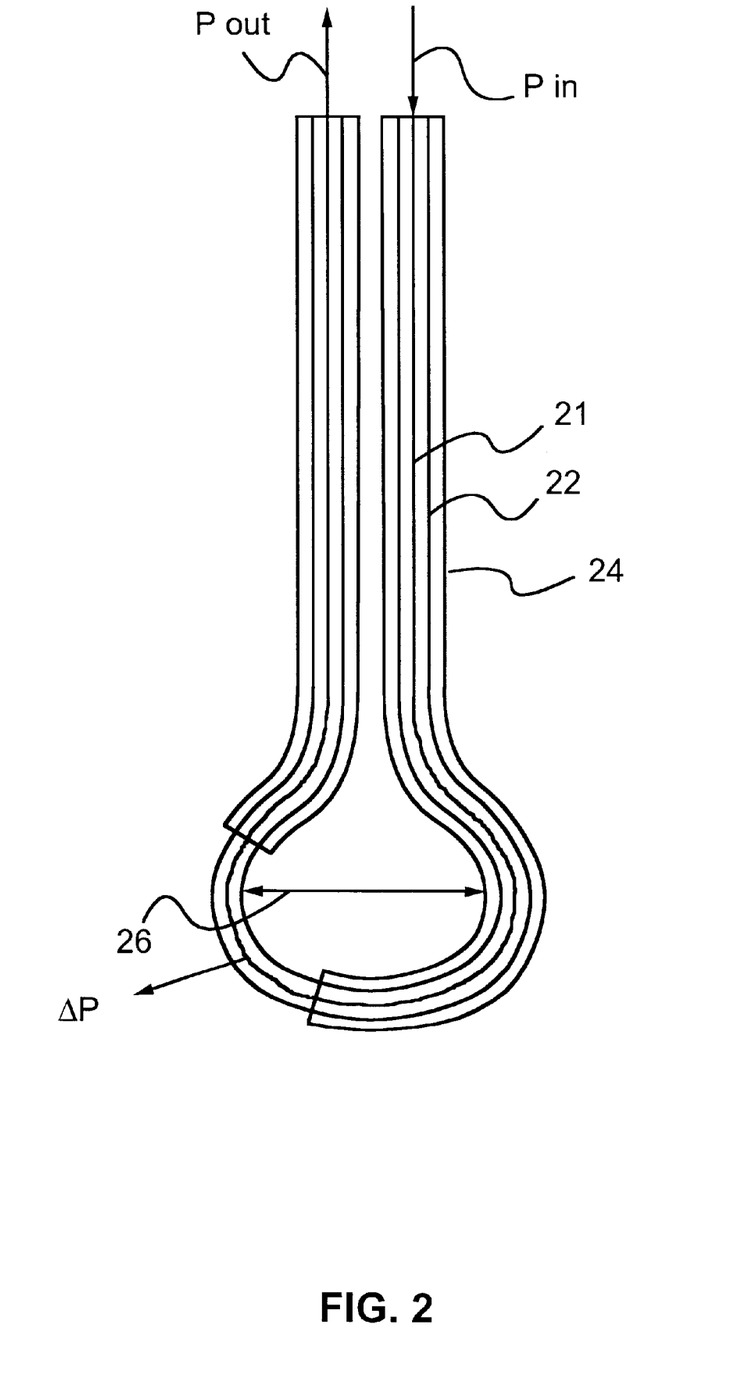
FIG. 2 is a diagram of the environmental media sensor.
Figure 3:
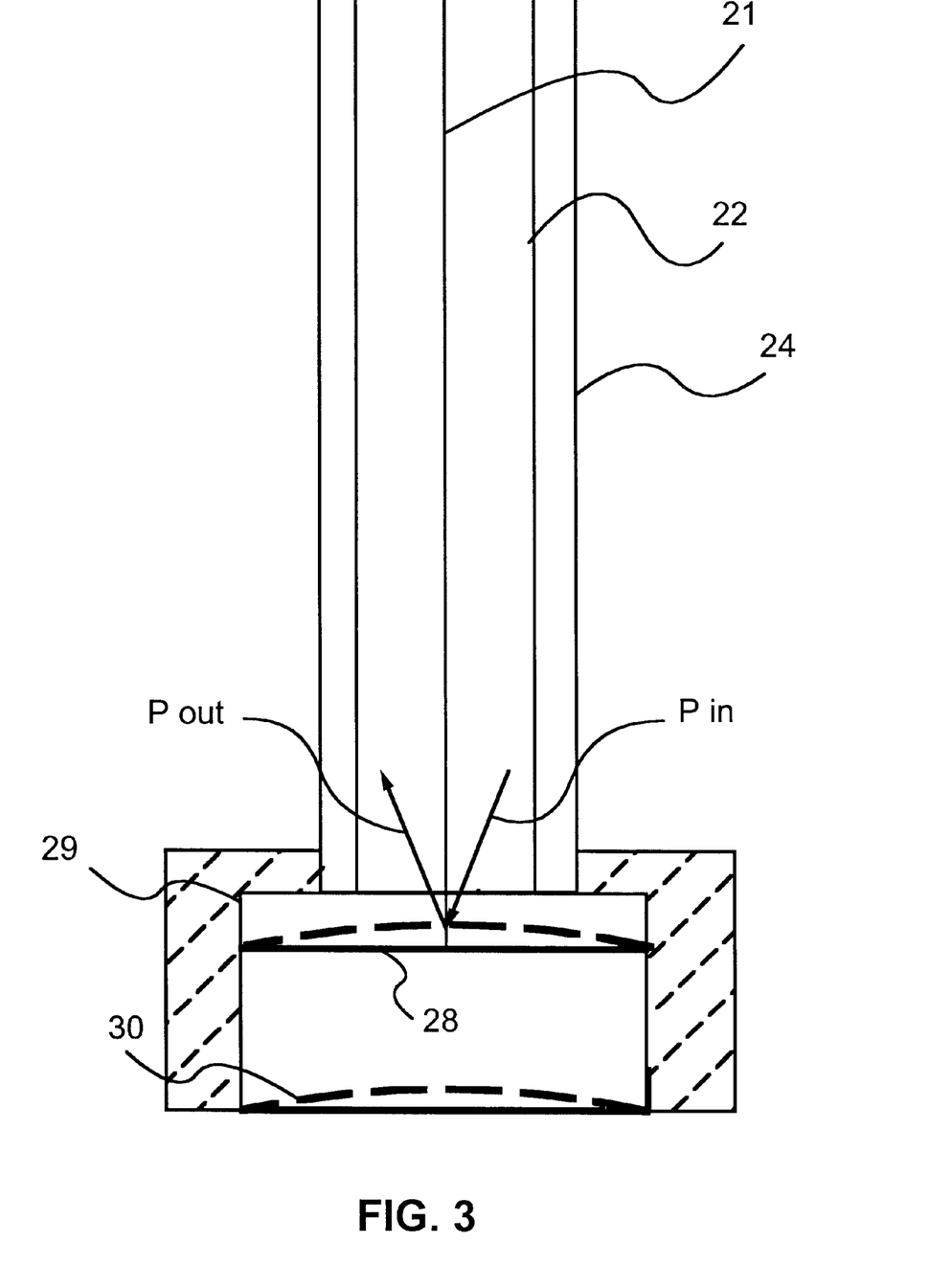
FIG. 3 is a diagram of the environmental pressure sensor.

The optical fiber used can be a single optical fiber, a bundle of optical fibers, a cable of optical fibers, or a tube of optical fibers. In the preferred embodiment, a single optical fiber with a diameter of 100 $\mu$m is used. The optical fiber, as shown in FIGS. 2 and 3, consists of a core 21 through which light travels, a cladding 22, and a jacket 24. Jacket 24 is of an opaque material that allows light traveling within the fiber to be almost completely internally reflected so that it cannot pass out of the fiber. Likewise, light outside of jacket 24 cannot pass into core 20.

The fiber is attached at one end to a light source, such as a laser, an LED, or another type of light source delivering e.g., white light, UV light, or IR light. Different fibers can be used for different light sources. Between the fiber and the light source, there may be a lens which can focus the light into the optical fiber. The light is emitted at a known intensity or power.

At the other end, the fiber is attached to a light detector, such as a photo multiplier tube or a charge coupled device. Between the fiber and the light detector, there may be a lens which can focus the light on the light detector. The light detector measures the intensity of the light after it has traveled through the length of the optical fiber. Thus any changes between the intensity of the light emitted and the intensity of light detected can be easily calculated. To obtain the maximum sensitivity and stability the light source is modulated and synchronized detection techniques are used. These methods are well-known to a person of average skill in the art.

The environmental media sensor is located between the light source and the light detector. In the preferred embodiment, as in FIG. 2, this sensor comprises a loop of optical fiber with a diameter of ⅜ inches 26. Diameter 26 has been found to provide the sensor with the highest sensitivity and the lowest amount of stress. Diameter 26 may be altered, however, to produce a specific result for certain media. The amount of light that is lost is determined by the degree of curvature of the loop. Jacket 24 is removed from this loop of optical fiber, so that light traveling within core 21 may pass through cladding 22 to the outside. Cladding 22 may also be removed to further increase this effect, although this will render the fiber more fragile.

The amount of light, and corresponding amount of power, that is lost also depends on the medium in which the fiber is placed. As is well known, light travels at different speeds in different media. This characteristic is symbolized by the angle of refraction, or refractive index n. Light travels slower in media with higher n. This translates into a change in the amount of light lost via transmission through the cladding. For example, light travels slower in water (n=1.5) than in air (n=1.0). If the unjacketed fiber illustrated in FIG. 2 is placed in a container of water, the amount of light lost will be larger than the amount of light lost if the fiber was placed in air. Thus, the amount of light lost from the optical fiber due to transmission increases in direct proportion to the refractive index of the medium in which the fiber is placed.

Figure 4:
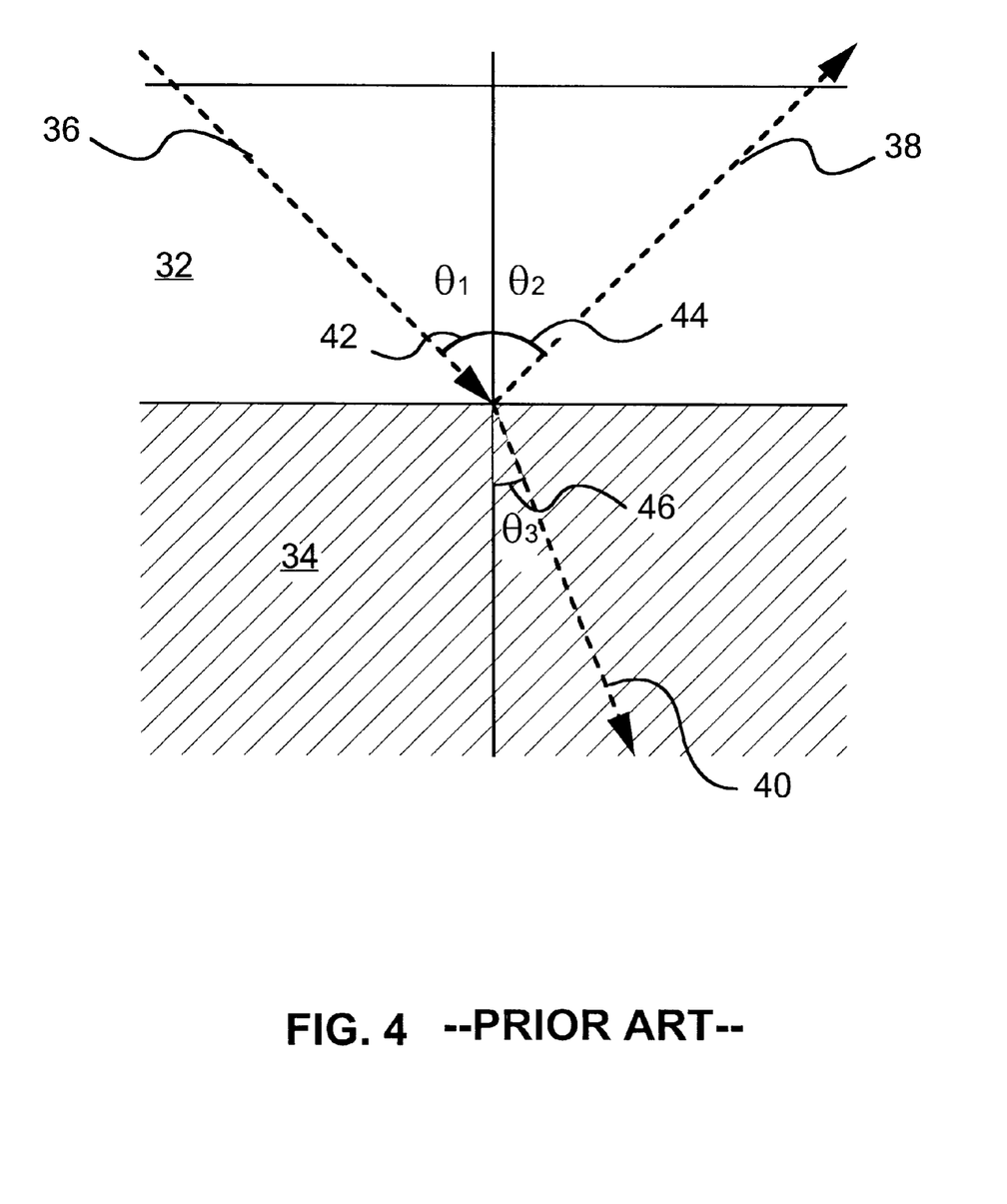
FIG. 4 is a diagram of the reflection and transmission of a beam of light at the interface of two media with different refractive indexes.

FIG. 4 illustrates this phenomenon. The incident light ray 36 is traveling through the unjacketed fiber, as shown in FIG. 2. Incident light ray 36 encounters the interface between the air 32 in the unjacketed fiber and the second medium 34, which has a higher refractive index. Incident light ray 36 hits the interface at an angle $\theta_1$. Part of it is reflected as a reflected light ray 38 at the same angle $\theta_2 (\theta_1=\theta_2)$. Reflected light ray 38 does not have the same intensity as incident light ray 36, however, because some of incident light ray 36 is transmitted through second medium 34. The transmitted light ray 40 is refracted at a different angle $\theta_3$ because of the second medium's higher index of refraction. Thus, after traveling a certain length of unjacketed optical fiber which has been placed in a specific medium, incident light beam 36 will have lost a certain amount of power.

The resulting light intensity can be measured by the light detector at the other end of the fiber. The difference between the intensity of the light emitted and the intensity of the light detected is easily calculated. This difference corresponds to the medium in which the fiber was placed. Thus, one value may indicate the sensor has been placed in water, while another value may indicate the sensor has been placed in gasoline. In the preferred embodiment, as shown in FIG. 1, the light source and the light detector are connected to the environmental media display, which clearly shows the calculated value and corresponding media.

The media recognition channel determines the value and corresponding media. This is illustrated in FIG. 5, where I=power in and R=power out. In the first operation, the difference between I and R (I−R) is calculated. This number is then divided by I ((I−R)/I) in the next operation. The resulting value is then matched by a computer 48 against value sets of different media, such as air, water, or gasoline. If the value matches a value set, it is amplified by an amplifier 49 and the media is definitively identified on display 50.

Different media also have different densities. Water, for example, is much denser than air, and as such exerts more pressure on objects placed on or within it. Even similar substances, such as water and gasoline, display different pressures under the same conditions at the same depth. This characteristic can thus be used to identify different media within the same container. A step-wise change in pressure roughly indicates where the two media meet.

A second optical fiber contains the pressure sensor, as shown in FIG. 3. This sensor consists of the end of an optical fiber containing a mirror 28 and a flexible membrane 30, ideally made of silicon. Light travels the length of the optical fiber, is reflected off mirror 28, and returns to the light detector. Membrane 30 is fully deformable and is thus distorted under the pressure of the media. When membrane 30 is moved, mirror 28 located above it near the end of the optical fiber is also moved into the empty space 29. As a result, light traveling through the optical fiber will undergo a certain amount of scattering. The return light thus has a different intensity than it had previously, before membrane 30 and mirror 28 were moved, as can be seen by $P_{in}$ and $P_{out}$. This difference corresponds to a pressure reading.

Figure 6:
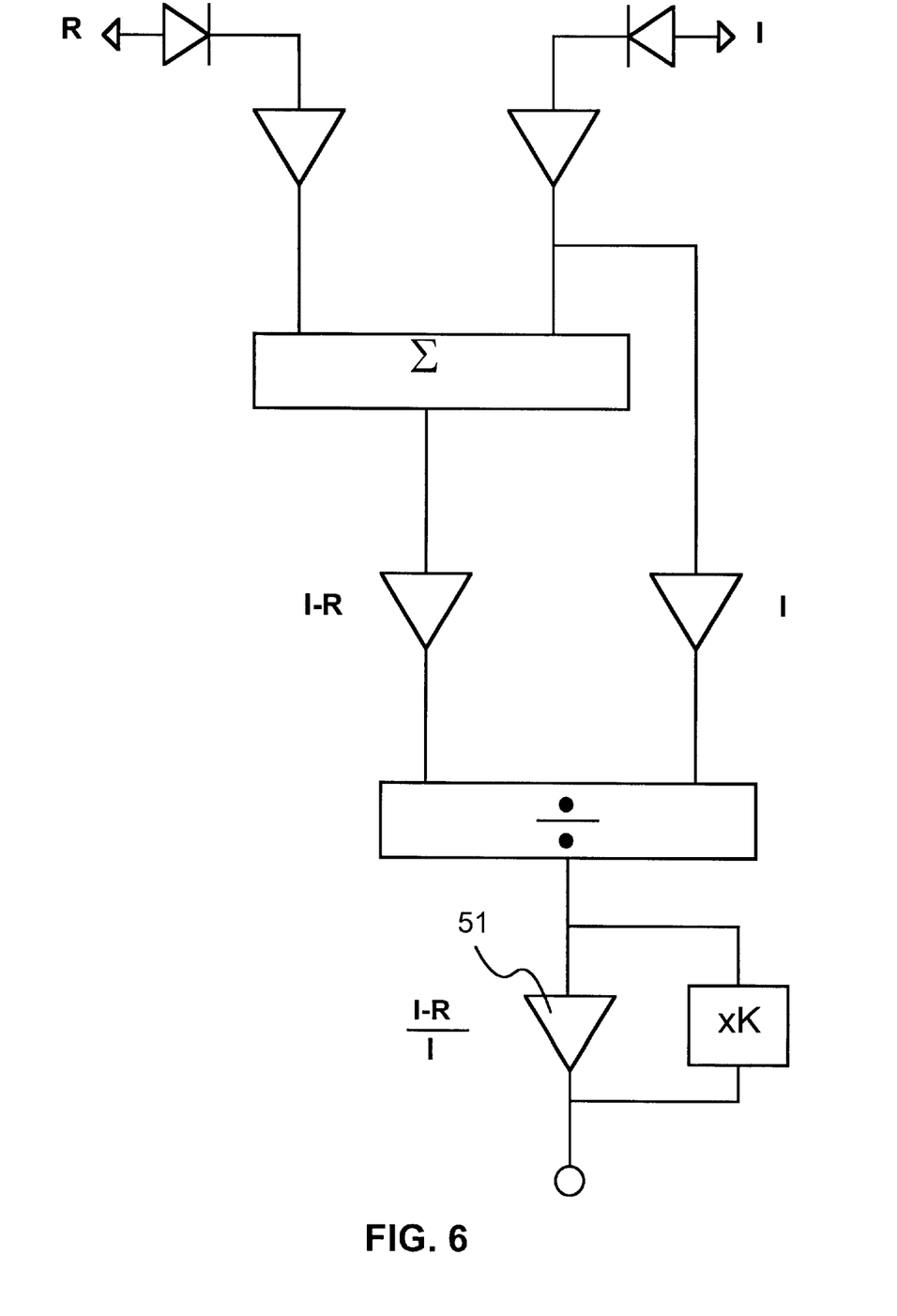
FIG. 6 is a diagram of the pressure measurement channel.

The pressure measurement channel determines the difference. This is illustrated in FIG. 6, with I=power in and R=power out. In the first operation, the difference between I and R (I−R) is calculated. This number is then divided by I ((I−R)/I in the next operation. The resulting value represents a corresponding pressure which amplified by an amplifier 51 and then displayed to the user.

Figure 7:
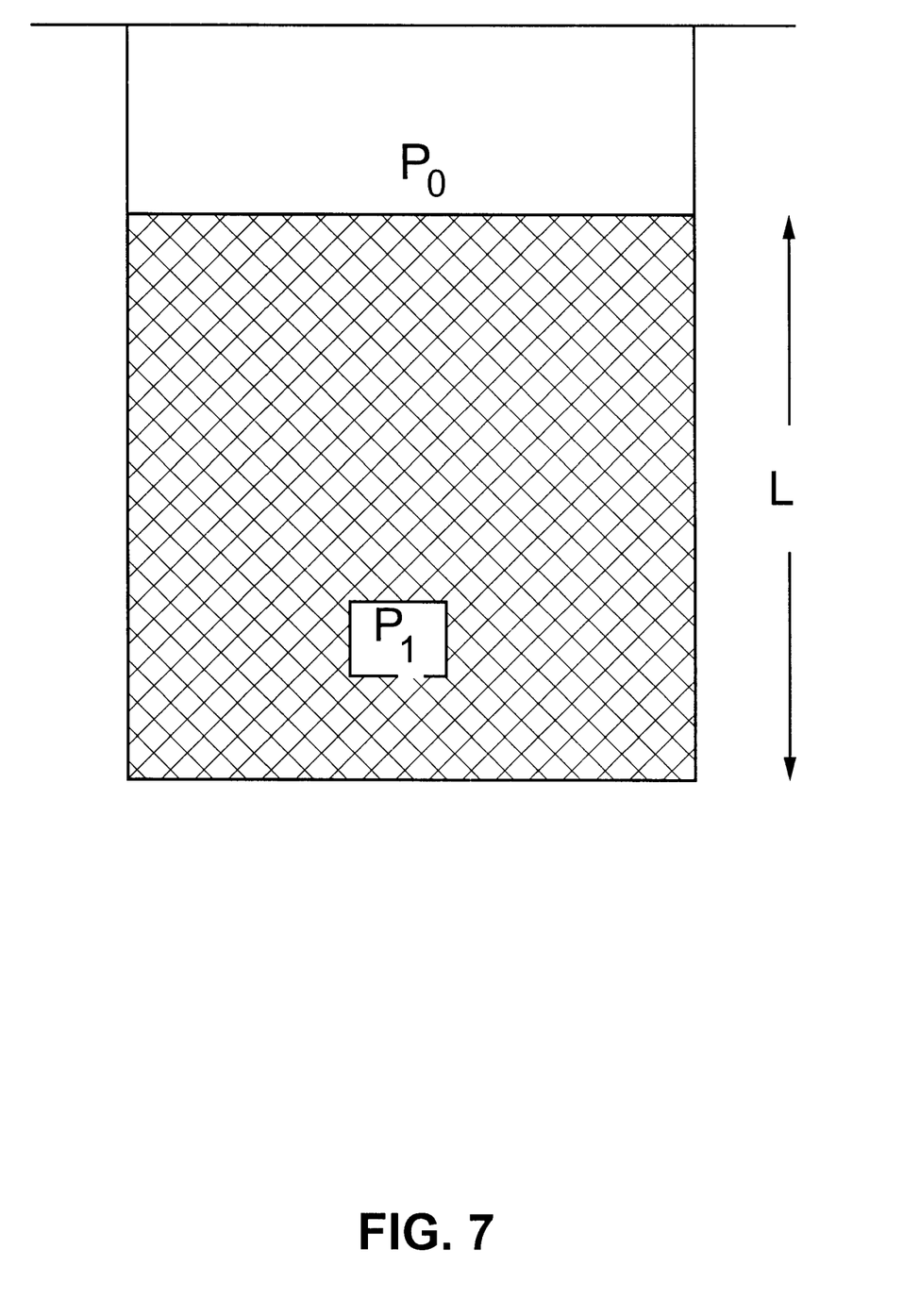
FIG. 7 is a diagram of a container holding a fluid with atmospheric and applied pressures indicated.

The pressure reading can also be used to determine the level of a medium in a container, such as tank 64. As shown in FIG. 7, the top of the media has a pressure $P_o$ (atmospheric pressure), which is a known value. At the bottom of tank 64 the media has a pressure $P_1$ (applied pressure), which is calculated by the environmental pressure sensor. The level of the media can be determined using the equation $L=(P_1-P_o)/gQ$, where g=gravity and Q=density of the media. The value of Q is constant for a substance. Once the medium recognition channel has identified the media, the value of Q can be found and used in calculating L. The level of a media can be continuously calculated. Clearly, the continuous calculation allows one to perform level measurements on media containing several components, i.e., media mixtures, since the detector can track all the media which make up the mixture. In this case the above equation has to be modified to measure level L while taking into account all media recorded by the detector during its continuous measurement.

The pressure sensor may take a variety of forms. In one embodiment, the sensor may branch off the main optical fiber, forming a Y shape. The light source and light detector are still placed at either end of the main optical fiber and the media sensor is still located on the main optical fiber between the source and detector. The light from the main optical fiber is deflected down into the pressure sensor, and then from the sensor back to the main optical fiber. In another embodiment, the sensor is located at the end of one of the main optical fibers while the media sensor is located on the other one. The light source and light detector are placed in the same location or even in the same housing. For the media sensor, the light source is attached to one end of the optical fiber and the light detector is attached to the other end. For the pressure sensor, the light source and light detector are located at the same end of the optical fiber. Either embodiment is effective.

The present invention allows for networking between the pressure measurement channel and the environmental media channel. The information from one can influence the gathering of the information by the other. One sensor obtains information which is sent to its respective channel. This channel interprets the information, and depending on the received information, sends a signal to the second sensor, requesting new information. New information obtained by the second sensor is sent to its respective channel, which then sends it to the first channel. The process can be repeated continuously, or until all necessary information has been gathered. For example, if the level of gasoline drops below the level detectable by the sensor device, the pressure measurement channel will see a big change in the pressure of the media. It can then request updated information from the media sensor to confirm that the media has changed from gasoline to air. The media sensor will send the information to the environmental media channel, which will then relay the information to the pressure measurement channel.

Figure 8:
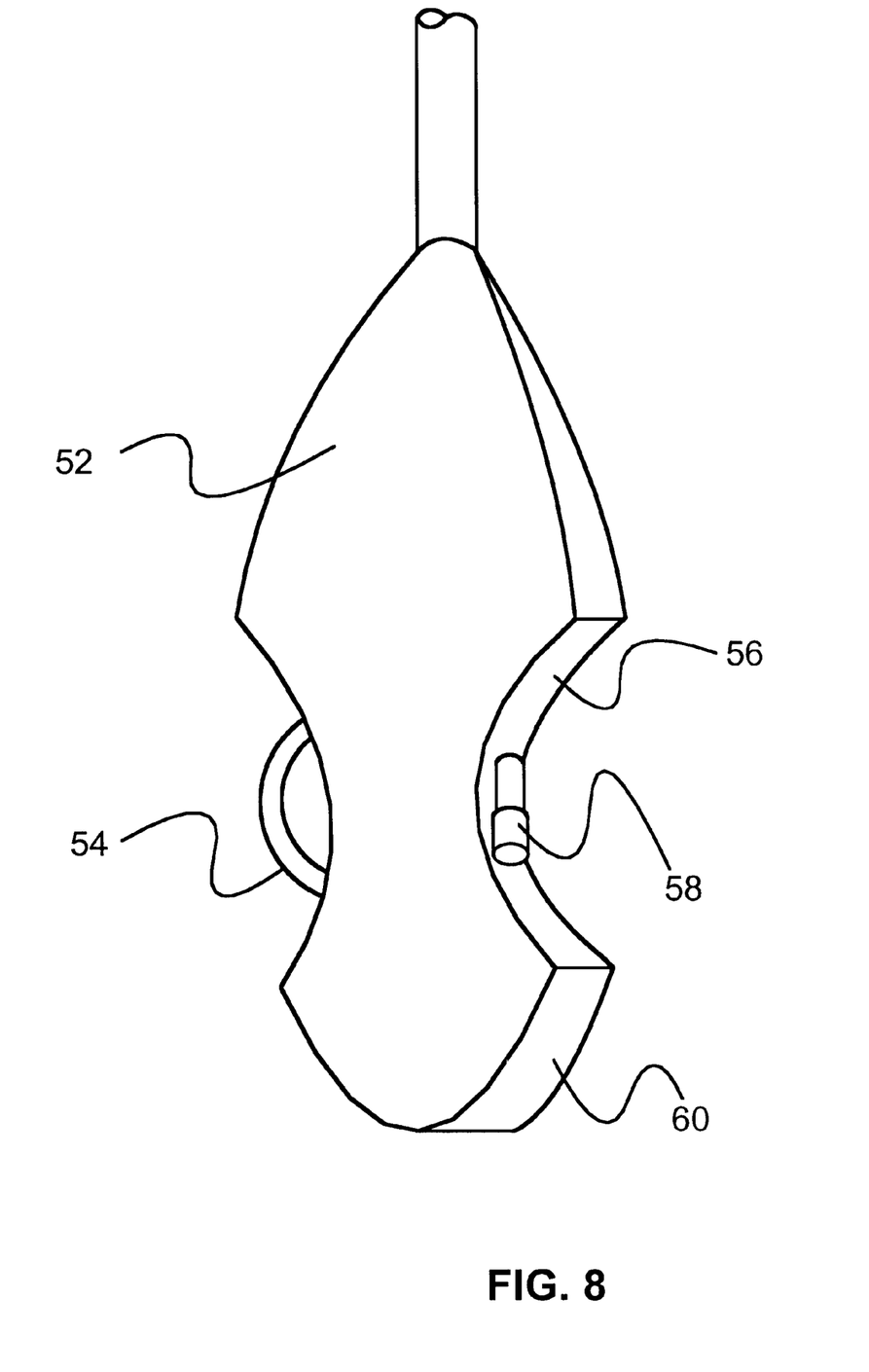
FIG. 8 is an illustration of the housing comprising two protective recessed grooves for the media sensor and pressure sensor.

The invention also includes a housing 52 for both sensors. In the preferred embodiment, as shown in FIG. 8, housing 52 has a violin shape, with one curved end surface 60. Curved surface 60 is superior to a sharp surface because it reduces the amount of damage to both the sensor devices 56, 58 and housing 52 holding the media to be measured. Housing 52 has on its sides protective convex grooves 54, one for each sensor. Sensors 56, 58 are located inside grooves 54, reducing the chance of damage by outside objects while still allowing sensors 56, 58 to have full contact with the media. The full function of sensors 56, 58 is unaffected by grooves 54 and overall housing 52.

It will be clear to one skilled in the art that the above embodiment may be altered in many ways without departing from the scope of the invention. For example, more than one sensor could be used to identify and determine the pressure of more than one type of media in the same container. Or the housing could have other means of protecting the sensors, such as differently shaped grooves. Accordingly, the scope of the invention should be determined by the following claims and their legal equivalents.

What is claimed is:

1. A method for identifying a medium in a mixture of media and determining a level of said mixture of media by using a detector having a light source for providing a light and a light detector for receiving said light, said method comprising the following steps:

a) providing a first light path for said light between said light source and said light detector through a first optical fiber;

b) providing a media sensor in said first optical fiber for continuously monitoring medium identity through contact inducing a first change in the intensity of said light;

c) providing a second light path for said light between said light source and said light detector through a second optical fiber;

d) providing a pressure sensor for continuously monitoring pressure through contact inducing a second change in the intensity of said light;

e) mounting said media sensor and said pressure sensor in a housing and lowering said housing into said mixture of media such that said pressure sensor and said media sensor continuously monitor at the same sensing depth;

f) identifying media interfaces using said pressure sensor; and g) providing a means for networking information from said media sensor and said pressure sensor for determining the level of said mixture of media.

2. The method of claim 1, wherein said step of identifying media interfaces comprises identifying a step-wise pressure change.

3. The method of claim 1, wherein said means for networking information verifies a change of media by comparing a pressure reading from said pressure sensor with a medium identity reading from said media identity sensor.

4. The method of claim 3, wherein said comparing step is performed when said networking means receives a step-wise pressure change reading from said pressure sensor.

5. The method of claim 3, wherein said comparing step is performed when said networking means receives a media identity change reading from said media identity sensor.

6. The method of claim 1, wherein said mounting step comprises mounting said media identity sensor in a first recess and mounting said pressure sensor in a second recess.

7. The method of claim 6, wherein said first recess and said second recess are provided at the same height.

8. The method of claim 6, wherein said first recess and said second recess are arcuate.

9. The method of claim 1, wherein said contact between said media mixture and said pressure sensor produces a deformation of said pressure sensor which causes said second change in the intensity of said light.

10. The method of claim 1, wherein said contact between said media mixture and said media identity sensor produces a leakage of said light which causes said first change in the intensity of said light.

* * * * *